United States Patent
Cabral

[19]

[11] Patent Number: 6,059,455
[45] Date of Patent: *May 9, 2000

[54] PORTABLE X-RAY BONE DENSITOMETRY SYSTEM

[75] Inventor: Richard E. Cabral, Tewksbury, Mass.

[73] Assignee: Hologic, Inc., Waltham, Mass.

[*] Notice: This patent is subject to a terminal disclaimer.

[21] Appl. No.: 08/484,572

[22] Filed: Jun. 7, 1995

Related U.S. Application Data

[63] Continuation-in-part of application No. 08/345,069, Nov. 25, 1994, which is a continuation-in-part of application No. 08/156,287, Nov. 22, 1993, Pat. No. 5,432,834.

[51] Int. Cl.[7] ..................................................... H05G 1/02
[52] U.S. Cl. ........................... 378/196; 378/195; 378/198
[58] Field of Search ................................... 378/195, 196, 378/197, 198, 208, 209, 177, 178, 179

[56] References Cited

U.S. PATENT DOCUMENTS

| | | |
|---|---|---|
| 3,803,417 | 4/1974 | Kok . |
| 3,944,830 | 3/1976 | Dissing . |
| 3,988,585 | 10/1976 | O'Neill et al. . |

(List continued on next page.)

FOREIGN PATENT DOCUMENTS

| | | |
|---|---|---|
| 0026494 | 4/1981 | European Pat. Off. . |
| 0432730 | 6/1991 | European Pat. Off. . |
| 0461028 | 12/1991 | European Pat. Off. . |
| 0713676 | 5/1996 | European Pat. Off. . |
| 2238706 | 2/1974 | Germany . |
| WO8607531 | 12/1986 | WIPO . |
| WO9421174 | 9/1994 | WIPO . |

OTHER PUBLICATIONS

Lunar, A Quantum Leap in Bone Densitometry, Expert, The World's First Imaging Densitometer (undated but beleived to have been published before Nov. 22, 1992).

Lunar News, Dec. 1992, "Lunar Introduces Expert, the World's First Imaging Densitometer".

Product Information, Expert, Today's Breakthrough—Tomorrow's Standard (undated, but believed to have been published before Nov. 22, 1993).

Hanson, L., et al., "Preliminary Evaluation of a New Imaging Bone Densitometer," Presented at the Fourth International Symposium on Osteoporosis, Mar. 27–31, 1993, Hong Kong.

Performance Comparison: Multiple vs. Single Beam X–ray Bone Densitometry, Hologic , Inc. Sep. 1992.

Lunar DP3 User's Manual, Dual–Photon Scanner, pp. 4, 8, 10 and 22 (undated).

Nucletron, A New Dimension In Dual–Photon Absorptiometry, Brochure, Novo Diagnostic (undated).

(List continued on next page.)

*Primary Examiner*—Don Wong
*Attorney, Agent, or Firm*—Cooper & Dunham LLP

[57] ABSTRACT

A portable x-ray bone densitometry system is suitable for transportation between rooms of a medical facility through generally standard doorways. The system has a base portion capable of rolling ambulation by at least one human operator during transportation and selective stabilization on a floor for patient scanning. The apparatus has a patient table extending parallel to a Y-axis of an XYZ coordinate system for supporting a patient at a patient position. The patient table includes a central portion coupled with the base portion, and at least one table leaf coupled with the table central portion, for extending table length parallel to the Y-axis. The apparatus also has a source-detector support coupled with the base portion; an x-ray source, coupled with the source-detector support, for emitting a beam of x-rays to irradiate at any one time a scan line which is transverse to the Y-axis; and an x-ray detector, coupled with the source-detector support arm in alignment with the source at opposite sides of the patient table along a source-detector axis which is transverse to the Y-axis, for receiving x-rays from the source after passage thereof through the patient position. A scanning mechanism moves at least one of the patient table and the source-detector support relative to the other to scan the patient position with the x-ray beam. The patient table may have a pair of leaves attached to the central portion with hinges at opposite ends thereof.

16 Claims, 1 Drawing Sheet

U.S. PATENT DOCUMENTS

| | | |
|---|---|---|
| 4,144,457 | 3/1979 | Albert . |
| 4,358,856 | 11/1982 | Stivender et al. . |
| 4,365,343 | 12/1982 | Grady et al. . |
| 4,649,560 | 3/1987 | Grady et al. . |
| 4,715,057 | 12/1987 | Hahn et al. . |
| 4,716,581 | 12/1987 | Barud . |
| 4,788,429 | 11/1988 | Wilson . |
| 4,811,373 | 3/1989 | Stein . |
| 4,829,549 | 5/1989 | Vogel et al. . |
| 4,903,203 | 2/1990 | Yamashita et al. . |
| 4,977,588 | 12/1990 | Van der Ende ............ 378/195 |
| 5,040,199 | 8/1991 | Stein . |
| 5,070,519 | 12/1991 | Stein . |
| 5,132,995 | 7/1992 | Stein . |
| 5,148,455 | 9/1992 | Stein . |
| 5,155,756 | 10/1992 | Pare et al. . |
| 5,165,410 | 11/1992 | Warne et al. . |
| 5,172,695 | 12/1992 | Cann et al. . |
| 5,177,776 | 1/1993 | Ohmori et al. . |
| 5,228,068 | 7/1993 | Mazess . |
| 5,287,546 | 2/1994 | Tesic et al. . |
| 5,291,537 | 3/1994 | Mazess . |
| 5,305,368 | 4/1994 | Bisek et al. . |
| 5,306,306 | 4/1994 | Bisek et al. . |
| 5,432,834 | 7/1995 | Gershman ............... 378/146 |

OTHER PUBLICATIONS

The Norland Model 2600 Dichromatic Bone Densitometer Brochure, Norland Corp. (undated).

"DPA gaining strength in bone scanning debate", Diagnostic Imaging, Jun. 1986, pp. 102–108.

Osteotek Brochure, models 200 and 300, Medical & Scientific Enterprises, Inc. (undated).

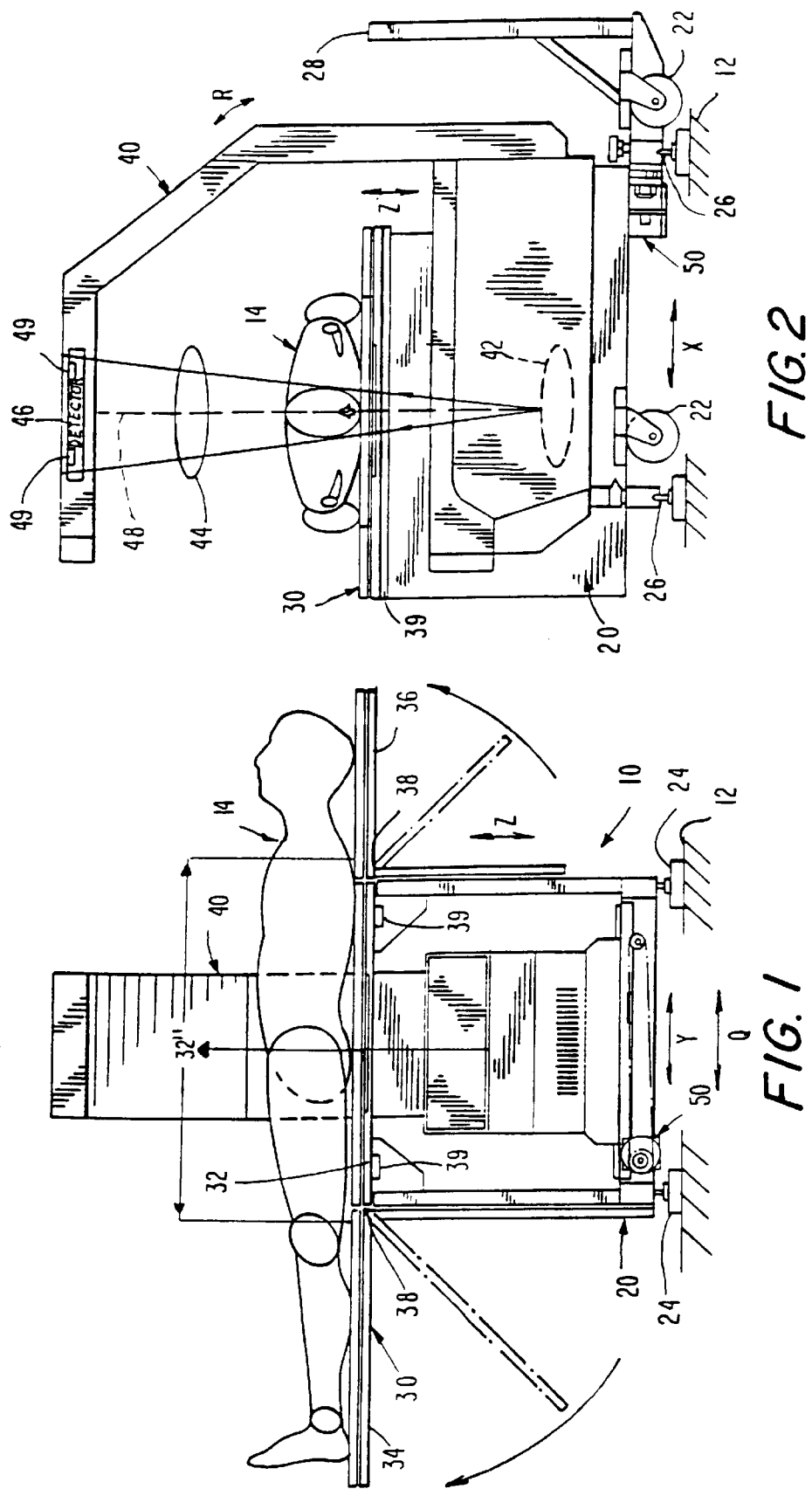

PORTABLE X-RAY BONE DENSITOMETRY SYSTEM

REFERENCE TO RELATED APPLICATIONS

This application is a continuation-in-part of parent application Ser. No. 08/345,069, filed on Nov. 25, 1994, which in turn is a continuation-in-part of application Ser. No. 08/156,287, filed on Nov. 22, 1993, now U.S. Pat. No. 5,432,834, both of which are hereby incorporated by reference herein as though fully set forth herein.

BACKGROUND AND SUMMARY OF THE INVENTION

The invention relates to portable x-ray based bone densitometry systems and methods and techniques useful at least in such systems and methods.

X-rays or gamma-rays can be used to measure the density and distribution of bone in the human body in order to help health professionals assess and evaluate projected bone mineral density, which in turn can be used to monitor age-related bone loss that can be associated with diseases such as osteoporosis.

In bone densitometry, a patient typically is placed on a table such that the patient's spine extends along the length of the table, along a direction that can be called the Y-axis in Cartesian coordinates. For a supine patient, the left and right sides are in a direction typically called the X-axis. A source at one side of the patient transmits radiation through the patient to a radiation detector at the other side. The source and the detector typically are mechanically linked by a structure such as a C-arm to ensure their alignment along a source-detector axis which is transverse (typically perpendicular) to the Y-axis. The detector in a fan beam-type system typically is an elongated array of detector elements arranged along a line or an arc. By means of mechanically moving the C-arm and/or moving the table, a region of interest in a patient on the table can be scanned with the radiation.

Typical regions of analysis in bone densitometry include the spine, hip, forearm, and wrist, scanned individually. They can be covered individually within a reasonable time by a fan beam that has a relatively narrow angle in a single pass or, alternatively, by a pencil beam scanning a raster pattern. Another analysis region is termed "oblique hip" in which the hip is viewed at an angle relative to the horizontal and vertical directions. Another analysis region is referred to as "whole body" in which the entire patient body is scanned and analyzed for bone density and possibly also for "body composition" or the percentages of fat and muscle in the body.

X-ray bone densitometry systems have been made by the owner of this application under the tradenames QDR-2000+, QDR-2000, QDR-1500, QDR-1000plus, and QDR-1000. The following commonly owned U.S. patents pertain to such systems and are hereby incorporated by reference herein: U.S. Pat. Nos. 4,811,373, 4,947,414, 4,953,189, 5,040,199, 5,044,002; 5,054,048, 5,067,144, 5,070,519, 5,132,995 and 5,148,455; and 4,986,273 and 5,165,410 (each assigned on its face to Medical & Scientific Enterprises, Inc. but now commonly owned). Other bone densitometry systems are believed to have been made by the Lunar Corporation of Madison, Wis. (see, e.g., the system which is believed to be offered under the tradename Expert and U.S. Pat. Nos. 5,228,068, 5,287,546 and 5,305,368, none of which is admitted to be prior art against this invention). It is believed that other manufacturers also have offered bone densitometry products.

It would be advantageous, in many instances, to have an X-ray bone densitometry system for the measurement of bone density, that is easily transportable with a minimum of setup. Ideally, the system apparatus would be capable of going through standard doorways with no disassembly. In the United States of America, doorways for medical buildings typically are 36 inches (0.91 meters) wide.

While portable shadowgraph-type x-ray radiography systems, which can be transported through standard doorways, are available for hospitals, nursing homes, medical clinics and physician medical offices, portable densitometry systems have not been available to the medical community. Part of the reason has no doubt been that the C-arm structures and motorized patient tables used in known bone densitometry systems are bulky and have required relatively large floor footprints and clearance in order for those systems to achieve their full range of scanning motions.

It is an object of the present invention to create a portable bone densitometry system having an examination table unit, which in fully assembled, but in partially collapsed form can be passed through a doorway having a width of 36 inches (0.91 m).

It is another object of the present invention to create a portable bone densitometry system which is fully self-contained, i.e., does not require disassembly or reassembly before passing through doors and which does not require component re-alignment after transportation.

It is also an object of the present invention to create a system of x-ray bone densitometers, with each unit comprising the system having different scanning motion capabilities from purely Y-axis-only scanning motion along at least part of the length of a patient on the patient table, to complete X-, Y- and Z-axis scanning motions, including rotation of the C-arm source-detector support about a rotational axis which is parallel to the Y-axis of the patient table.

The portable bone densitometry system of the present invention achieves the aforementioned objects of small linear dimensions for passage through doorways, self containment and minimum setup time in order to become operational at multiple locations.

The portable x-ray bone densitometry system of the present invention is suitable for transportation between rooms of a medical facility through generally standard doorways. The system has a base portion capable of rolling ambulation by at least one human operator during transportation and selective stabilization on a floor for patient scanning. The apparatus has a patient table extending parallel to a Y-axis of an XYZ coordinate system for supporting a patient at a patient position. The patient table includes a central portion coupled with the base portion, and at least one table leaf coupled with the table central portion, for extending table length parallel to the Y-axis. The apparatus also has a source-detector support coupled with the base portion; an x-ray source, coupled with the source-detector support, for emitting a beam of x-rays to irradiate at any one time a scan line which is transverse to the Y-axis; and an x-ray detector, coupled with the source-detector support arm in alignment with the source at opposite sides of the patient table along a source-detector axis which is transverse to the Y-axis, for receiving x-rays from the source after passage thereof through the patient position. A scanning mechanism moves at least one of the patient table and the source-detector support relative to the other to scan the patient position with the x-ray beam. The patient table may have a pair of leaves attached to the central portion with hinges at opposite ends thereof.

BRIEF DESCRIPTION OF THE DRAWINGS

A more complete understanding of the invention may be obtained from the following description when taken in conjunction with the drawings, in which:

FIG. 1 is a front elevational view of mechanical subsystems of any embodiment of the invention.

FIG. 2 is a side elevational view of mechanical subsystems of an embodiment of the invention of FIG. 1.

DESCRIPTION OF PREFERRED EMBODIMENTS

Referring to FIGS. 1 and 2, a scanning system 10 has a base portion 20, including castered wheels 22 for ambulation of the system 10 within a medical facility. When the system 10 is transported to a desired location for performing patient scans, extendable stabilization and levelling pads 24 are extended toward the floor 12 by rotation of adjustment screws 26, in order to provide a stable, non-shaking scanning platform. The stabilization pads 24 are retracted prior to subsequent movement of the scanning system 10. Handle 28 is attached to the base portion 20 for operator movement of the densitometry system 10.

A patient 14 is supported on a patient table unit 30 that is coupled with the base portion 20. The patient table 30 has a central portion 32 and a pair of table leaves 34, 36 which are coupled with the central portion with hinges 38. The leaves 34, 36 may be dropped to a vertical, space-saving position, as shown in phantom in FIG. 1.

When the table leaves 34, 36 are dropped vertically, the remaining total scanner system length measured parallel to the Y-axis is only 32 inches (0.81 m), in order to fit through a standard 36 inch doorway, as is typically available at clinics, hospitals, nursing homes and other medical facilities. The table 30 central portion 32 may also be mounted to the base portion 20 by manually-operated table slides 39, which allow manual movement of the table 30 parallel to the X- and Y- axes.

The central portion 32 of the table 30 has an x-ray translucent inset panel through which the scanning takes place. The leave extensions themselves 34, 36 can be constructed of x-ray translucent materials or any other structurally suitable material. Each table section is preferably fitted with a foam pad for patient comfort.

C-arm 40 serves as a source-detector support, and is coupled to the base portion 20. The system 10 has electro-mechanical components, control systems and other components involved in performing a patient scan and acquiring scan data.

A patient 14 can lie in the supine position during scanning on patient table unit 30. X-rays from an x-ray source 42 located beneath table 30 pass through patient 14 and are received by a detector 46, which is aligned with respect to the source 42 along a source-detector axis 48. The detector 46 has an array of detector elements 49 located above patient 14. Each detector element 49 responds to x-rays at respective angular positions within a fan beam 44 of x-rays. Both x-ray source 42 and detector 46 are supported on C-arm 40 which maintains a selected source-to-detector distance and alignment.

C-arm 40 rotates essentially within its own volume along rotational path R about a rotational axis extending along the Y-axis. In addition, C-arm 40 moves along the Y-axis, along the length of a patient and thus along the patient's spine. The Y-axis and the Q-axis extend in the same direction.

Patient support table 30 is translatable along all three axes—the longitudinal (Y axis), the transverse (X axis), and the vertical (Z axis). As seen in FIG. 1, table 30 can be driven in the positive and in the negative directions along the Y-axis by using a scanning mechanism 50. C-arm 40 moves in conjunction with patient table 30. The motion of table 30 makes it possible to achieve a more compact C-arm rotation volume. Each motion is computer controlled and monitored by an absolute encoder feedback system receiving feedback information from an absolute encoder as described in the parent applications incorporated by reference herein.

The portable scanner system 10 has a fully self-contained integral design. That is to say that the apparatus does not require any disassembly or component realignment between moves as is now required of such equipment. It has the "plug in and run" features as would be expected of portable equipment. The system 10 apparatus maintains x-ray source 42 and detector array 46 in alignment.

The scanner system 10 of the present invention can be supplied with varying degrees of automated scan motion control. While the system 10 described above is capable of many kinds of automated relative motion between the table 30 and the source-detector support 40, other less automated systems can be provided which practice the present invention. In a minimal automation, portable scanner system design, the only relative scanning motion can be accomplished by movement of the source-detector support 40 along a single scan path, and the angle of the fan beam 44 relative to the table surface would remain fixed in the central position shown in FIG. 2. In such a minimally configured system, the patient 14 could be manually slid on sheets and adjusted to fall within the scan area and repositioned manually to scan other areas of the anatomy.

As a slightly upgraded portable system 10, the table central portion 32 at least slides forward and back, parallel to the X-axis on the manual slides 39. This manual slide system 39 would be used for patient loading and further would allow for intermediate patient positions in the X direction for spine to hip repositioning.

The in manual-position scanner systems, the apparatus shown scans along the length of the patient in the patient long axis only and is the only motorized axis (axis Q). The fan beam 44 is wide enough at the patient 14 to provide sufficient beam width in the X direction for scanning a width through the patient that encompasses the patient's entire spine width or hip area. Therefore, the X motion is not required to be a motorized scanning motion. It merely requires manual repositioning of the patient on the table to go from a spine scan, hip scan or further along the spine etc.

Scanning system 10 also includes a workstation (not shown) which controls the examination table unit 30 and C-arm 40, and processes scan data into forms more useful for diagnostic purposes, such as into patient images and reports. The workstation is described in greater detail in copending parent applications Ser. Nos. 08/345,069 and 08/156,287, which are incorporated herein by reference as if fully set forth herein.

The workstation can be mounted on a separate rolling computer-type cart or it can be integrated with the base portion 20, thus reducing the apparatus to a single rolling hardware assembly.

While a preferred embodiment of the invention has been described in detail, it should be understood that changes and variations will be apparent to those skilled in the art which are within the scope of the invention recited in the appended claims.

What is claimed is:

1. A portable x-ray bone densitometry system comprising:
   a base portion capable of rolling ambulation by at least one human operator during transportation and selective stabilization on a floor for patient scanning;
   a patient table for supporting a patient at a patient position, the patient table having:
      a central portion coupled with the base portion; and
      at least one table leaf coupled with the table central portion, the at least one table leaf being movable between a space-saving position and an extended position relative to the base portion to extend the table length beyond the base and parallel to a Y-axis of an XYZ coordinate system;
   a source-detector support coupled with the base portion;
   an x-ray source, coupled with the source-detector support, for emitting a beam of x-rays to irradiate at any one time a scan line which is transverse to the Y-axis;
   an x-ray detector, coupled with the source-detector support arm in alignment with said source at opposite sides of the patient table along a source-detector axis which is transverse to the Y-axis, for receiving x-rays from the source after passage thereof through the patient position; and
   a scanning mechanism capable of moving the patient table and the source-detector support relative to the other when scanning the patient position with said x-ray beam.

2. A portable x-ray bone densitometry system comprising:
   a wheeled base portion capable of rolling ambulation by at least one human operator during transportation and selective stabilization with adjustable stabilization pads on a floor for patient scanning;
   a patient table extending parallel to a Y-axis of an XYZ coordinate system for supporting a patient at a patient position, the patient table having:
      a central portion coupled with the base portion; and
      at least one table leaf coupled with the table central portion for extending the table length parallel to the Y-axis;
   a source-detector support coupled with the base portion such that the support and base portion are in a fixed linear relationship;
   an x-ray source coupled with the source-detector support, for emitting a beam of x-rays to irradiate at any one time a scan line which is transverse to the Y-axis;
   an x-ray detector coupled with the source-detector support arm in alignment with said source at opposite sides of the patient table along a source-detector axis which is transverse to the Y-axis, for receiving x-rays from the source after passage thereof through the patient position; and
   a scanning mechanism capable of moving the patient table and the source-detector support relative to the other when scanning the patient position with said x-ray beam.

3. A portable x-ray bone densitometry system comprising:
   a base portion capable of rolling ambulation by at least one human operator during transportation and selective stabilization on a floor for patient scanning;
   a patient table extending parallel to a Y-axis of an XYZ coordinate system for supporting a patient at a patient position, the patient table having:
      a central portion coupled with the base portion; and
      at least one table leaf coupled with the table central portion, for extending the table length parallel to the Y-axis;
   a source-detector support coupled with the base portion such that the support and base portion are in a fixed linear relationship;
   an x-ray source coupled with the source-detector support arm, for emitting a narrow angle fan beam of x-rays to irradiate at any one time a scan line which is transverse to the Y-axis and is substantially shorter than the width of a body cross-section of a typical adult patient occupying the patient position;
   an x-ray detector coupled with the source-detector support arm in alignment with said source at opposite sides of the patient table along a source-detector axis which is transverse to the Y-axis, for receiving x-rays from the source within the angle of said fan beam after passage thereof through the patient position, the detector comprising a number of detecting elements arranged along a direction transverse to the Y-axis and to the source-detector axis; and
   a scanning mechanism capable of moving the patient table and the source-detector support relative to the other when scanning the patient position with the narrow angle fan beam in successive scans parallel to the Y-axis in which the source-detector axis is at different angles relative to the patient position as between different ones of said successive scans.

4. The system of claim 1, wherein the at least one table leaf includes a pair of table leaves coupled with the table central portion at opposite ends thereof.

5. The system of claim 1, wherein the table leaf is coupled with the patient table central portion by hinges and is movable to a vertically-oriented position.

6. The system of claim 1, wherein the base portion has wheeled casters and extendable stabilization pads.

7. The system of claim 1, wherein the patient table central portion is fixed relative to the base portion and the scanning mechanism translates the source-detector support parallel to the Y-axis.

8. The system of claim 1, wherein the patient table central portion is fixed relative to the base portion and the scanning mechanism translates the source-detector support parallel to the X-axis.

9. The system of claim 1, wherein the patient table central portion translatable relative to the base portion and the scanning mechanism translates the central portion parallel to the Z-axis.

10. The system of claim 1, wherein the patient table central portion translatable relative to the base portion, the scanning mechanism translates the central portion parallel to the Z-axis, and the source-detector support may be pivoted about an axis through the x-ray source focal spot point of origin.

11. The system of claim 1, wherein:
    the patient table central portion is translatable relative to the base portion; and
    the scanning mechanism translates the central portion parallel to at least the X- and Z-axes, and rotates the source-detector support on an axis parallel to the Y-axis, but not through the x-ray source focal spot point of origin.

12. The system of claim 11, wherein the source-detector support rotates within its own volume.

13. The system of claim 1, wherein the patient table central portion is mounted to the base portion on manual slides for selective motion thereof parallel to at least one of the X- and Y-axes.

14. A portable x-ray bone densitometry system comprising:

a base portion capable of rolling ambulation by at least one human operator during transportation and selective stabilization on a floor for patient scanning the base portion defining a system length measure parallel to a y-axis of an xyz coordinate system which is sufficient to permit transportation of the system through standard doorways;

a patient table for supporting a patient at a patient position, the patient table having:
 a central portion coupled with the base portion and dimensioned within the system length; and
 at least one table leaf coupled with the table central portion, the at least one table leaf being moveable between a space-saving position within the system length and an extended position relative to the base portion to extend the table length beyond the system length and parallel to the Y-axis;

a source-detector support coupled with the base portion;

an x-ray source coupled with the source-detector support, for emitting a beam of x-rays to irradiate at any one time a scan line which is transverse to the Y-axis;

an x-ray detector coupled with the source-detector support arm in alignment with said source at opposite sides of the patient table along a source-detector axis which is transverse to the Y-axis, for receiving x-rays from the source after passage thereof through the patient position; and a scanning mechanism capable of moving the patient table and the source-detector support relative to the other when scanning the patient position with said x-ray beam.

15. The system of claim 14, wherein the standard doorway is a 36 inch doorway.

16. The system of claim 14, wherein the system length is at least 32 inches.

* * * * *

UNITED STATES PATENT AND TRADEMARK OFFICE
CERTIFICATE OF CORRECTION

PATENT NO. : 6,059,455
DATED : May 9, 2000
INVENTOR(S) : Richard E. Cabral

It is certified that error appears in the above-identified patent and that said Letters Patent is hereby corrected as shown below:

Title page,
Item [75], add -- Russell J. Gershman, Lexington, Massachusetts --

Signed and Sealed this

Eleventh Day of December, 2001

*Attest:*

NICHOLAS P. GODICI
*Attesting Officer*    *Acting Director of the United States Patent and Trademark Office*